(12) United States Patent
Kang et al.

(10) Patent No.: US 9,173,841 B2
(45) Date of Patent: Nov. 3, 2015

(54) POLYMER NANOPARTICLE INJECTION FORMULATION COMPOSITION CONTAINING RAPAMYCIN WITH IMPROVED WATER SOLUBILITY, PREPARATION METHOD THEREOF, AND ANTICANCER COMPOSITION FOR COMBINED USE WITH RADIOTHERAPY

(71) Applicant: SAMYANG BIOPHARMACEUTICALS CORPORATION, Seoul (KR)

(72) Inventors: Hye Won Kang, Namyangju-si (KR); Min Hyo Seo, Daejeon (KR); Sa Won Lee, Daejeon (KR); Bong Oh Kim, Daejeon (KR); Eun Kyung Choi, Seoul (KR); Seong Yun Jeong, Seoul (KR); Ha Na Woo, Seoul (KR)

(73) Assignee: SAMYANG BIOPHARMACEUTICALS CORPORATION, Seoul (KR)

( * ) Notice: Subject to any disclaimer, the term of this patent is extended or adjusted under 35 U.S.C. 154(b) by 0 days.

(21) Appl. No.: 14/231,355

(22) Filed: Mar. 31, 2014

(65) Prior Publication Data
US 2014/0212462 A1    Jul. 31, 2014

Related U.S. Application Data

(62) Division of application No. 13/519,914, filed as application No. PCT/KR2010/009476 on Dec. 29, 2010, now abandoned.

(30) Foreign Application Priority Data

Dec. 30, 2009    (KR) .................. 10-2009-0134617

(51) Int. Cl.
A61K 9/14    (2006.01)
A61K 9/00    (2006.01)
(Continued)

(52) U.S. Cl.
CPC .................. A61K 9/14 (2013.01); A61K 9/0019 (2013.01); A61K 9/127 (2013.01); A61K 31/436 (2013.01)

(58) Field of Classification Search
CPC ....... A61K 9/14; A61K 9/0019; A61K 9/127; A61K 31/436
See application file for complete search history.

(56) References Cited

U.S. PATENT DOCUMENTS

| 5,530,006 | A | 6/1996 | Waranis et al. |
| 7,311,901 | B2 | 12/2007 | Seo et al. |

(Continued)

FOREIGN PATENT DOCUMENTS

| EP | 0 650 730 A1 | 5/1995 |
| JP | 2008-535927 A | 9/2008 |

(Continued)

OTHER PUBLICATIONS

International Search Report, issued in PCT/KR2010/009476, dated Sep. 15, 2011.

(Continued)

*Primary Examiner* — Trevor Love
(74) *Attorney, Agent, or Firm* — Birch, Stewart, Kolasch & Birch, LLP

(57) ABSTRACT

The present invention relates to a polymer nanoparticle injection formulation composition containing rapamycin with improved water solubility, and more specifically, to an injection formulation composition containing rapamycin wherein water solubility is improved by solubilizing rapamycin having low water solubility with polymer nanoparticles, a preparation method thereof, and an anticancer composition for a combined use with radiotherapy.

9 Claims, 8 Drawing Sheets

(51) Int. Cl.
*A61K 9/127* (2006.01)
*A61K 31/436* (2006.01)

(56) References Cited

U.S. PATENT DOCUMENTS

| 8,349,306 | B2 | 1/2013 | Seo et al. |
| 2004/0253195 | A1 | 12/2004 | Seo et al. |
| 2005/0201972 | A1 | 9/2005 | Seo et al. |
| 2008/0152616 | A1 | 6/2008 | Seo et al. |

FOREIGN PATENT DOCUMENTS

| WO | WO 2005/060361 A2 | 7/2005 |
| WO | WO 2005/107813 A1 | 11/2005 |
| WO | 2006/110862 A2 | 10/2006 |
| WO | WO 2008/109163 A1 | 9/2008 |

OTHER PUBLICATIONS

Yanez et al., "Pharmacometrics and delivery of novel nanoformulated PEG-b-poly(ε-caprolactone) micelles of rapamycin", Cancer Chemotherapy and Pharmacology, Jan. 2008, vol. 61, No. 1, pp. 133-144.

Murphy, J.D. et al., "Inhibition of mTOR Radiosensitizes Soft Tissue Sarcoma and Tumor Vasculature," Clinical Cancer Research, Jan. 15, 2009, vol. 15, No. 2, pp. 589-596.

Wang, Z. M. et al., "Advances of Molecular Targeted Therapy for Malignant Gliomas," Chinese Cancer, 2006, vol. 15, pp. 158-162, and concise explanation of relevance.

Duration of treatment (Day)

POLYMER NANOPARTICLE INJECTION FORMULATION COMPOSITION CONTAINING RAPAMYCIN WITH IMPROVED WATER SOLUBILITY, PREPARATION METHOD THEREOF, AND ANTICANCER COMPOSITION FOR COMBINED USE WITH RADIOTHERAPY

CROSS REFERENCE TO RELATED APPLICATIONS

This application is a Division of U.S. patent application Ser. No. 13/519,914, filed on Jun. 29, 2012, which is the U.S. National Stage of PCT/KR2010/009476, filed on Dec. 29, 2010. This application claims the benefit of priority of 10-2009-0134617, filed in Korea on Dec. 30, 2009. The entire contents of all of the above applications is hereby incorporated by reference.

TECHNICAL FIELD

The present invention relates to an injectable composition comprising polymeric nanoparticles containing rapamycin with an improved water solubility, more specifically, to an injectable composition containing rapamycin wherein the poorly water-soluble rapamycin is solubilized with polymeric nanoparticles and its water solubility is improved thereby, and a method for preparing the same, and an anticancer composition comprising the same for a combination therapy with radiation.

BACKGROUND ART

Rapamycin (molecular formula: $C_{51}H_{79}NO_{13}$, molecular weight: 914.2), also known as sirolimus, is a macrolide lactone-based compound. It has an immunosuppressive activity and so has been commercialized as a transplant rejection inhibitor (Rapamune) for organ transplant patients. As well as for inhibiting the organ transplant rejection, rapamycin can be used for treating pulmonary inflammation, systemic lupus erythematosis, immunoinflammatory skin disorders including psoriasis, immunoinflammatory bowel disorders, ocular inflammation, restenosis, rheumatoid arthritis, etc.

Recently, it has been reported that in addition to the function of the immunosuppressive agent, rapamycin has the function of an anticancer agent which acts as an inhibitor of mammalian target of rapamycin (mTOR) to induce apoptosis and destroy cancer cells thereby. However, since rapamycin has a very low solubility in water (1 to 2 μg/ml), it shows a very low absorption rate upon oral administration and has a great variance in bioavailability between individuals.

Rapamune tablet has been introduced as a formulation containing rapamycin. This tablet comprises excipients including sucrose, lactose, polyethylene glycol 8000, calcium sulfate, microcrystalline cellulose, povidone, poloxamer 188, glyceryl monooleate, etc. In addition, Rapamune oral solution comprises Phosal 50 PG (phosphatidyl choline, propylene glycol, mono-glyceride, di-glyceride, ethanol, soy bean fatty acid, ascorbyl palmitate) and polysorbate 80, with 1.5 to 2.5% of ethanol content.

When Rapamune oral solution is orally administered to human patients, the absolute bioavailability is about 14%. When Rapamune tablet is orally administered, the absolute bioavailability is relatively higher by about 25% as compared with the oral administration Rapamune oral solution. However, both formulations show low absolute bioavailability below 20% and this is due to the low solubility of rapamycin in water.

Therefore, various attempts have been made to formulate rapamycin using various solubilization techniques. U.S. Pat. No. 5,559,121 discloses a capsule formulation composition containing a solution of rapamycin wherein rapamycin is dissolved in a mixed solution comprising polysorbate 80 surfactant, N,N-dimethylacetamide, and either lecithin or phospholipid. U.S. Pat. No. 5,616,588 discloses an injectable aqueous solution of rapamycin wherein rapamycin is dissolved in an aqueous solution of propylene glycol at a concentration of 0.1 to 4 mg/ml, without containing non-ionic surfactant. However, the known injectable aqueous solutions of rapamycin have a poor stability as an aqueous solution and thus should be administered within a short period of time. No injectable formulations are commercially available at present.

Korean Patent No. 0160957 discloses a composition for inhibiting organ or tissue transplant rejection, which comprises rapamycin in an effective amount for inhibiting mammalian organ or tissue transplant rejection. However, in this patent, rapamycin is used together with oils such as olive oil, alcohols, propylene glycols, and polyethylene glycols and surfactants such as Cremophor EL and polysorbate 80.

As a technique for solubilizing poorly soluble drugs, U.S. Pat. Nos. 6,322,805 and 6,616,941 disclose a polymeric micelle using an amphiphilic block copolymer in which a hydrophilic polyethylene glycol (A) block and a hydrophobic polylactide (B) block are combined in the form of an A-B type diblock. However, no specific examples to solubilize rapamycin with said polymeric micelle have been provided therein.

DETAILED DESCRIPTION

Technical Purpose

The present invention is to solve the problems involved in the prior arts as stated above. The technical purpose of the present invention is to provide an injectable composition comprising polymeric nanoparticles containing rapamycin—the composition containing no organic solvent, having good biocompatibility, using a biodegradable polymeric material only and injectable via intravenous or subcutaneous/intramuscular route—and a method for preparing the same, and an anticancer composition comprising the same for a combination therapy with radiation.

Technical Solution

To achieve the above-mentioned technical purposes, the present invention provides an injectable composition comprising polymeric nanoparticles containing rapamycin, the composition comprising: (i) an A-B type diblock copolymer having a hydrophilic block (A) and a hydrophobic block (B), (ii) an alkali metal salt of polylactic acid or its derivative having at least one carboxyl group on its end, and (iii) rapamycin as an active ingredient, wherein rapamycin is entrapped within the micelle formed from the A-B type diblock copolymer and the alkali metal salt of polylactic acid or its derivative.

In other aspect, the present invention provides a method for preparing an injectable composition comprising polymeric nanoparticles containing rapamycin, comprising the steps of: (a) solubilizing, in an organic solvent (i) an A-B type diblock copolymer having a hydrophilic block (A) and a hydrophobic block (B), (ii) an alkali metal salt of polylactic acid or its derivative having at least one carboxyl group on its end, and (iii) rapamycin as an active ingredient; (b) removing the organic solvent from the product of step (a); and (c) adding an aqueous medium to the product of step (b).

In another aspect, the present invention provides an anti-cancer composition for a combination therapy with radiation, comprising (i) an A-B type diblock copolymer having a hydrophilic block (A) and a hydrophobic block (B), (ii) an alkali metal salt of polylactic acid or its derivative having at least one carboxyl group on its end, and (iii) rapamycin as an active ingredient, wherein rapamycin is entrapped within the micelle formed from the A-B type diblock copolymer and the alkali metal salt of polylactic acid or its derivative.

Advantageous Effects

The injectable composition according to the present invention, after drying and when reconstituted in the aqueous solution, can provide an injectable solution having a solubility of rapamycin of 0.1 mg/ml or more. According to the present invention, an injectable composition of rapamycin—the composition capable of providing a solubility of rapamycin of 0.1 mg/ml or more, containing no organic solvent, having good biocompatibility, using a biodegradable polymeric material only and injectable via intravenous or subcutaneous/intramuscular route—can be obtained. When the composition of the present invention is administered in combination with radiotherapy, the effect of remarkably increasing the anticancer efficacy can be expected.

Since the present injectable composition containing rapamycin can maximize the effect of irradiation through synergistic action, it can reduce the radiotherapy-induced toxicity. Furthermore, rapamycin is a drug having potent pharmacological effects including immunosuppressive activity as well as radiation sensitizing activity, but also has serious side effects. In addition, since rapamycin is not dissolved in water, it should be formulated by using a solubilizing agent. The solubilizing agents currently used in the injection formulation are surfactants which mostly have toxicities such as hypersensitivity. However, the present injectable composition containing rapamycin causes no such toxicity of solubilizing agents and can exhibit the maximum radiation sensitizing effect while minimizing the dose of rapamycin and reducing the side effects.

MODE FOR INVENTION

Figure 1:
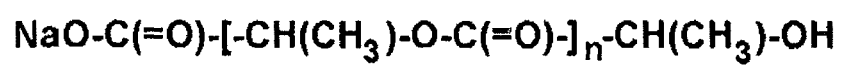
FIG. 1 is a NMR spectrum of D,L-PLA-COONa according to Preparation Example 1.
Figure 1:
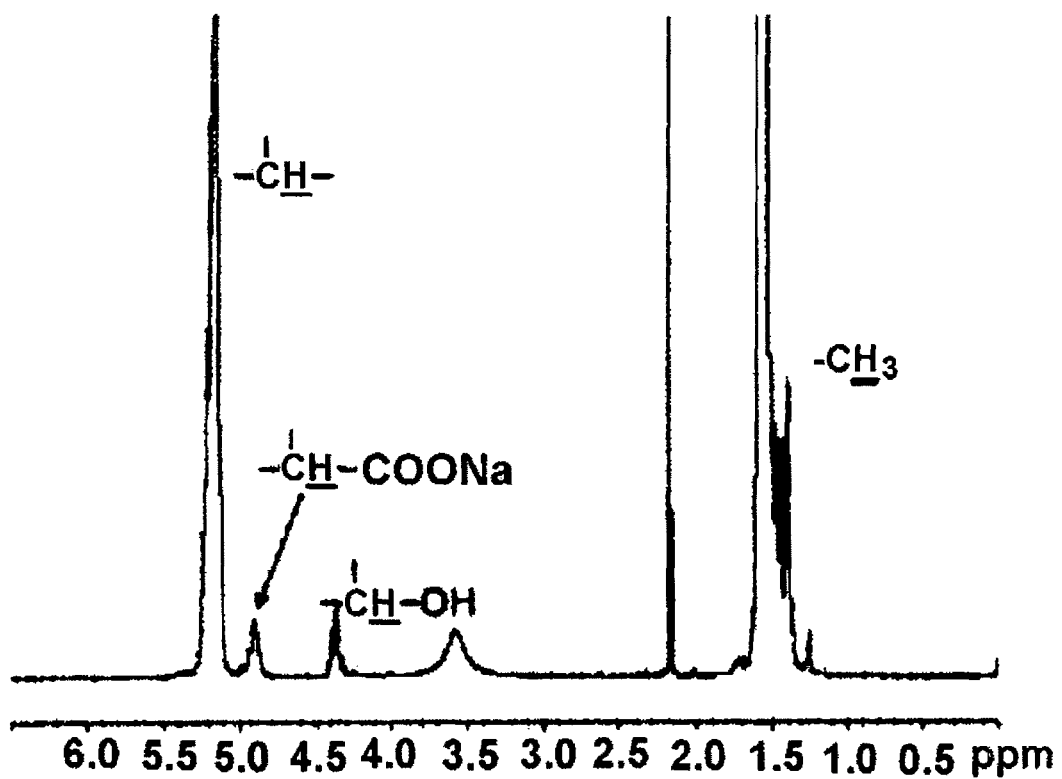

Hereinafter, the present invention will be described more specifically.

The term "rapamycin" as used herein includes all of rapamycin, its derivatives or analogs, and the pharmaceutically acceptable salts thereof. Rapamycin derivatives or analogs concretely include benzoyl rapamycin, everolimus, temsirolimus, pimetrolimus, violimus and the like, but not limited thereto. The term "nanoparticle" denotes the general concept referring to particles having a diameter of nanometer level, and includes micelle, mixed micelle, nanocapsule, nanosphere and the like, and the size thereof can be, for example, of 1 to 500 nm but not limited thereto.

In the present invention, the amphiphilic diblock copolymer (i) is an A-B type diblock copolymer having a hydrophilic block (A) and a hydrophobic block (B) wherein the hydrophilic block (A) can be polyethylene glycol and the hydrophobic block (B) can be polylactic acid or its derivative.

Polyethylene glycol for the hydrophilic block (A) can be polyethylene glycol, methoxy polyethylene glycol, etc. and concretely methoxy polyethylene glycol, but not limited thereto. The number average molecular weight of the hydrophilic block (A) is preferably 500 to 20,000 daltons, more preferably 1,000 to 10,000 daltons, and even more preferably 1,000 to 5,000 daltons. If the number average molecular weight of the hydrophilic block (A) is less than 500 daltons, the hydrophilic portion becomes smaller than the hydrophobic portion and thus the present composition may not be dissolved in water. If the number average molecular weight is greater than 20,000 daltons, the hydrophilic portion becomes too large and thus the micelle formation may be difficult. The content of the hydrophilic block (A) in the amphiphilic diblock copolymer is preferably 40 to 70 wt %, more preferably 50 to 65 wt %, on the basis of total 100 wt % of the diblock copolymer, in view of stable maintenance of the micelle of the amphiphilic diblock copolymer.

Polylactic acid or its derivative for the hydrophobic block (B) can be, for example, one or more selected from the group consisting of polylactic acid, polylactide, polyglycolide, polymandelic acid, polycaprolactone, polydioxan-2-one, polyamino acid, polyortho ester, polyanhydride and copolymers thereof, and more specifically polylactic acid, polylactide, polyglycolide, polymandelic acid, polycaprolactone or polydioxan-2-one. According to one embodiment of the present invention, polylactic acid or its derivative for the hydrophobic block (B) can be one or more selected from the group consisting of polylactic acid, polylactide, polycaprolactone, copolymer of lactic acid and mandelic acid, copolymer of lactic acid and glycolic acid, copolymer of lactic acid and caprolactone, and copolymer of lactic acid and 1,4-dioxan-2-one. The number average molecular weight of the hydrophobic block (B) is preferably 500 to 10,000 daltons, and more preferably 500 to 5,000 daltons. If the number average molecular weight of the hydrophobic block (B) is less than 500 daltons, the hydrophilic portion becomes too large and thus the micelle formation may be difficult. If the number average molecular weight is greater than 10,000 daltons, the hydrophobic portion becomes too large and thus the present composition may not be solubilized in water. The content of the hydrophobic block (B) in the amphiphilic diblock copolymer is preferably 30 to 60 wt %, more preferably 35 to 50 wt %, on the basis of total 100 wt % of the diblock copolymer, in view of stable maintenance of the micelle of the amphiphilic diblock copolymer.

In the present invention, the alkali metal salt of polylactic acid or its derivative having at least one carboxyl group on its end makes the inside of the drug-containing core of the micelle hard, and thus improves the inclusion efficiency of drug.

For the polylactic acid or its derivative having at least one carboxyl group on its end, one or more selected from the group consisting of polylactic acid, polylactide, polyglycolide, polymandelic acid, polycaprolactone, polyanhydride and copolymers thereof can be used. More specifically, the polylactic acid or its derivative can be polylactide, polyglycolide, polycaprolactone or copolymer thereof. According to a preferable embodiment of the present invention, polylactic acid or its derivative can be one or more selected from the group consisting of polylactic acid, copolymer of lactic acid and mandelic acid, copolymer of lactic acid and glycolic acid, and copolymer of lactic acid and caprolactone.

In the present invention, the alkali metal salt of polylactic acid or its derivative has a form wherein the terminal carboxylic acid anion of polylactic acid or its derivative is combined with the alkali metal ion via ionic binding. The alkali metal is one or more monovalent metals preferably selected from the group consisting of sodium, potassium and lithium, and is more preferably sodium. In the alkali metal salt of polylactic acid or its derivative, the other end—which is opposite to the carboxyl group ionically bound to alkali metal ion—can be substituted with one selected from the group consisting of hydroxy, acetoxy, benzoyloxy, decanoyloxy, palmitoyloxy and alkoxy.

Concretely, the alkali metal salt of polylactic acid having at least one carboxyl group on its end according to the present invention can be represented by the following chemical formula 1.

[Chemical Formula 1]

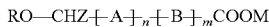

In the above formula,
A is

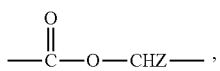

B is

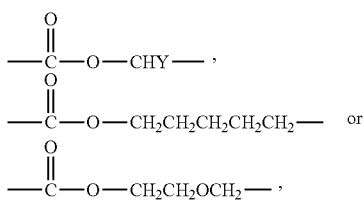

R is hydrogen, acetyl group, benzoyl group, decanoyl group, palmitoyl group, methyl group or ethyl group,
Z and Y are independently hydrogen, methyl group or phenyl group,
M is sodium, potassium or lithium,
n is an integer of 1 to 30, and
m is an integer of 0 to 20.

More concretely, the salt of polylactic acid or its derivative can be represented by the following chemical formula 2.

[Chemical formula 2]

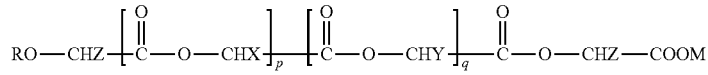

In the above formula,
R is hydrogen, acetyl group, benzoyl group, decanoyl group, palmitoyl group, methyl group or ethyl group,
X is methyl group,
Y' is hydrogen or methyl group,
Z is hydrogen, methyl group or phenyl group,
M is sodium, potassium or lithium,
p is an integer of 0 to 25, and
q is an integer of 0 to 25,
provided that p+q is an integer of 5 to 25.

The alkali metal salt of polylactic acid or its derivative shows preferably the water solubility of 20 mg/ml or more and, when dissolved in an aqueous medium, it participates in the micelle formation by achieving the balance between the hydrophilic portion of carboxylic acid anion and the hydrophobic portion of polylactic acid present in the molecule. Therefore, if the molecular weight thereof is too large, the hydrophobic portion becomes large such that the association between terminal carboxylic acid anions contributing to the hydrophilicity is difficult, by which the micelle may not be formed well. To the contrary, if the molecular weight thereof is too small, the alkali metal salt of polylactic acid or its derivative becomes completely dissolved in water and thus the micelle formation itself is to be difficult. According to a preferable embodiment of the present invention, the number average molecular weight of the alkali metal salt of polylactic acid or its derivative is 500 to 2,500 daltons, and particularly 1,000 to 2,000 daltons. If the molecular weight is less than 500 daltons, the alkali metal salt of polylactic acid or its derivative becomes completely dissolved in water and thus the micelle formation itself is to be difficult. If the molecular weight is greater than 2,500 daltons, the hydrophobicity is too great and the dissolution in an aqueous solution becomes difficult, and thus the micelle may not be formed.

According to a preferable embodiment of the present invention, the present injectable composition comprising polymeric nanoparticles containing rapamycin comprises 0.1 to 10 wt %, preferably 0.2 to 5 wt % of rapamycin, 40 to 90 wt %, preferably 45 to 74 wt % of the A-B type diblock copolymer having the hydrophilic block (A) and the hydrophobic block (B), and 10 to 50 wt %, preferably 25 to 45 wt % of the alkali metal salt of polylactic acid or its derivative having at least one carboxyl group on its end.

In an embodiment of the present invention, the weight ratio of the A-B type diblock copolymer and the alkali metal salt of polylactic acid or its derivative having at least one carboxyl group on its end is 9:1 to 3:7, and more concretely 5:1 to 1:2.

In case of forming the polymeric nanoparticle composition by mixing the amphiphilic block copolymer with the alkali metal salt of polylactic acid or its derivative, a divalent or trivalent metal ion can be further added in order to further improve the stability of nanoparticles. The divalent or trivalent metal ion is substituted for the terminal monovalent alkali metal cation of the alkali metal salt of polylactic acid or its derivative in the polymeric nanoparticle to form a stronger ionic bond with carboxyl group on the terminal of polylactic acid or its derivative.

Therefore, an embodiment of the present invention provides an injectable composition comprising polymeric nanoparticles containing rapamycin, comprising (i) the A-B type diblock copolymer having the hydrophilic block (A) and the hydrophobic block (B), (ii) the polylactic acid or its derivative comprising at least one carboxyl group on its end, the carboxyl group being fixed with the divalent or trivalent metal ion, and (iii) rapamycin as an active ingredient, wherein rapamycin is entrapped within the nanoparticle formed from the A-B type diblock copolymer and the polylactic acid or its derivative.

For the polylactic acid or its derivative comprising at least one carboxyl group on its end, those described above can be used.

The ionic bond with the divalent or trivalent metal ion acts to further improve the stability of polymeric nanoparticles through strong binding force. The divalent or trivalent metal ion is preferably a divalent or trivalent metal ion selected from the group consisting of calcium, magnesium, barium, chrome, iron, manganese, nickel, copper, zinc and aluminum, and more preferably a divalent cation of calcium or magnesium.

The equivalent of the divalent or trivalent metal ion can be adjusted, according to the release rate of the drug entrapped within polymeric nanoparticles. Concretely, if the divalent or trivalent metal ion is contained in the polymeric nanoparticle composition in an amount of less than 1 equivalent with respect to the equivalent of carboxyl group of the alkali metal salt of polylactic acid, the number of metal ion to be combined with carboxyl terminal group of polylactic acid salt is small and thus the release rate of drug increases. If the divalent or trivalent metal ion is contained in an amount of greater than 1 equivalent, the number of metal ion to be combined with carboxyl terminal group of polylactic acid salt is large and thus the release rate of drug decreases.

In case where the carboxyl terminal group of polylactic acid or its derivative is fixed with the divalent or trivalent metal ion, the composition of the present invention comprises preferably 0.1 to 10 wt %, more preferably 0.2 to 5 wt % of rapamycin; 40 to 90 wt %, more preferably 45 to 74 wt % of the amphiphilic block copolymer; and 10 to 50 wt %, more preferably 25 to 45 wt % of polylactic acid or its derivative having at least one carboxyl group on its end, on the basis of total weight of the composition, and further comprises 0.01 to 10 equivalent, more preferably 1 to 2 equivalent of the divalent or trivalent metal ion with respect to the equivalent of the terminal carboxyl group of polylactic acid or its derivative. If the relative proportion of the amphiphilic block copolymer is too large, the composition would have the properties of micelle, rather than the properties of polymeric nanoparticles and thus it may have a problem in stability when it is diluted. If the relative proportion of the metal salt of polylactic acid or its derivative is too large, the divalent or trivalent metal salt of polylactic acid or its derivative may be precipitated when the divalent or trivalent metal ion is added and thus uniformly dispersed nanoparticle solution may not be obtained.

As indicated above, the use of the divalent or trivalent metal ion can result in obtaining the composition in which the drug is entrapped within the nanoparticle comprising the amphiphilic block copolymer and polylactic acid or its derivative wherein carboxyl terminal group is fixed with the divalent or trivalent metal ion.

In an embodiment of the present invention, the composition of the present invention can be in a dry form prepared by lyophilization or spray drying. That is, the polymeric nanoparticle composition can be obtained in solid state by producing the micelle in an aqueous solution containing the above-mentioned components, and then drying the micelle by lyophilization, spray drying, etc. In case of the lyophilized composition, it can further comprise polysaccharides, mannitol, sorbitol, lactose, etc. as a protective agent for lyophilization. For the protective agent for lyophilization, preferably one or more selected from the group consisting of mannitol, sorbitol, lactose, trehalose and sucrose, and more preferably mannitol and lactose, can be used.

In the composition of the present invention, rapamycin is physically associated with the hydrophobic block portion of the polymer as explained above, and is located in the hydrophobic core of nanoparticles formed from the polymer in an aqueous solution, wherein the particle size of the rapamycin-containing polymeric nanoparticle is preferably in the range of 10 to 150 nm.

If the dry form of the composition according to the present invention is reconstituted in an aqueous medium, an injection formulation composition having the rapamycin concentration of 0.1 mg/ml or more, for example, 0.1 to 25 mg/ml and more concretely 0.2-10 mg/ml, can be obtained. If the rapamycin concentration is less than 0.1 mg/ml, the desired pharmacological effect of rapamycin cannot be attained. If the concentration is greater than 25 mg/ml, the viscosity of the aqueous solution at a temperature below room temperature becomes so high and thus its injection becomes difficult. In an embodiment, the injection formulation composition having the rapamycin concentration of 0.1 to 25 mg/ml is provided.

In addition to the above-mentioned components, the polymeric micelle injection formulation composition containing rapamycin according to the present invention can further contain one or more pharmaceutical additives such as preservative, stabilizing agent, wetting agent or emulsifying agent, salts and/or buffers for controlling osmotic pressure, etc., and other therapeutically useful materials. The injection formulation composition of the present invention can be administered via rectal, topical, percutaneous, intravenous, intramuscular, intraperitoneal, subcutaneous route, and the like. According to an embodiment of the present invention, the composition in a lyophilized form can be reconstituted with an aqueous medium such as water for injection, 5% glucose and physiological saline, and administered by intravenous injection.

Another aspect of the present invention provides a method for preparing an injectable composition comprising polymeric nanoparticles containing rapamycin, comprising the steps of: (a) solubilizing, in an organic solvent (i) an A-B type diblock copolymer having a hydrophilic block (A) and a hydrophobic block (B), (ii) an alkali metal salt of polylactic acid or its derivative having at least one carboxyl group on its end, and (iii) rapamycin as an active ingredient; (b) removing the organic solvent from the product of step (a); and (c) adding an aqueous medium to the product of step (b).

In the above step (a), the organic solvent can be preferably one or more selected from the group consisting of dichloromethane, ethanol, methanol, propanol, acetone, acetonitrile, 1,2-propylene glycol, N-methylpyrrolidone, N,N-diacetamide, polyethylene glycol or its derivative (molecular weight of 300 to 600 daltons), and glycerin.

In the above step (b), the removal of the organic solvent can be carried out by a conventional method. Concretely, it can be evaporated by using a vacuum evaporator.

In the above step (c), the aqueous medium can be distilled water, water for injection, physiological saline or aqueous solution of protective agent for lyophilization.

The method for preparing the polymeric nanoparticle composition containing rapamycin according to the present invention can further comprise, after step (c), the step of (c-1) adding divalent or trivalent metal ion to the product of step (c) in order to fix the terminal group of polylactic acid or its derivative further. For instance, an aqueous solution comprising the divalent or trivalent metal ion can be added to the aqueous solution of the polymer micelle obtained in step (c), and then the mixture can be stirred for 30 minutes or more at room temperature. The divalent or trivalent metal ion can be added in the form of sulfate salt, hydrochloride salt, carbonate salt, phosphate salt and hydrate. Concretely, calcium chloride, magnesium chloride, zinc chloride, aluminum chloride, ferric chloride, calcium carbonate, magnesium carbonate, calcium phosphate, magnesium phosphate, aluminum phosphate, magnesium sulfate, calcium hydroxide, magnesium hydroxide, aluminum hydroxide or zinc hydroxide can be added.

In addition, the method for preparing the polymeric nanoparticle composition containing rapamycin according to the present invention can further comprise the steps of: (d) sterilizing the polymeric nanoparticle composition obtained in step (c) or (c-1); (e) filling the sterilized aqueous solution of micelle in a suitable container in a constant amount; and (f) lyophilizing the filled container obtained in step (e). In the step (f), one or more selected from the group consisting of mannitol, sorbitol, lactic acid, trehalose and sucrose can be used as a protective agent for lyophilization. More concretely, mannitol can be used. In addition, after the lyophilization, the method can further comprise the step of (g) reconstituting the product with an aqueous medium such as distilled water, water for injection, physiological saline, etc. to obtain the injectable solution composition containing rapamycin.

Another aspect of the present invention provides an anticancer composition for a combination therapy with radiation, utilizing the polymeric nanoparticle composition containing rapamycin according to the present invention.

In case of a combination therapy of administration of the present anticancer composition of the present invention with the radiotherapy, rapamycin can be administered once at a dose of 30 mg/m$^2$ to 300 mg/m$^2$, and the radiation can be applied 5 times at a daily dosage of 80 Gy. In case of the anticancer composition of the present invention, it can be administered either by slow intravenous infusion or by subcutaneous or intramuscular injection.

In experiments using cancer-transplanted animals, the use of the polymeric nanoparticle composition according to the present invention in combination with radiation remarkably improves the effectiveness of the composition. For instance, the anticancer composition of the present invention can be administered at an interval of from minutes to weeks before or after the irradiation. In the method for administration, it is preferable to meaningfully prolong the time interval between the composition of the present invention and the radiotherapy. Accordingly, between the two therapies there may be an interval of days to weeks. The radiation useful in combination with the anticancer composition of the present invention includes, for example, γ-ray, X-ray (external beam), etc. In an embodiment of the present invention, the quantity of radiation to be irradiated can be in a range of from about 1 to about 100 Gy, concretely from about 5 to about 80 Gy, and more concretely from 10 to 50 Gy. The dose range for radioisotope can be determined according to the half-life of isotope and the intensity and kind of radiation as emitted.

According to an embodiment of the present invention, the anticancer composition for a combination therapy with radiation, which utilizes the polymeric nanoparticle composition containing rapamycin according to the present invention, can be administered at a timing of 1 minute to 7 days before irradiation.

According to another embodiment of the present invention, the anticancer composition for a combination therapy with radiation, which utilizes the polymeric nanoparticle composition containing rapamycin according to the present invention, can be used for the combination therapy wherein chemotherapy in combination with radiotherapy is practiced 1 to 5 times per week (for example, 1, 2, 3, 5 times per week) over a period of 4 to 12 weeks.

Another embodiment of the present invention provides a method for treating mammalian cancer cell with radiotherapy, wherein the injectable composition comprising polymeric nanoparticles containing rapamycin according to the present invention is administered at the time of, before or after irradiation to mammalian cancer cell, by which a sensitivity of mammalian cancer cell to radiotherapy can be increased.

Hereinafter, the present invention will be illustrated more specifically through Preparation Examples, Examples and Experiments. However, they are provided to explain the present invention only, and the scope of the present invention is not limited thereto.

Preparation Example 1

D,L-PLA-COONa (Number Average Molecular Weight: 1,200 Daltons)

The alkali metal salt of polylactic acid was prepared according to the known methods including those disclosed in Korean Patent Application No. 2002-0063955, etc. That is, 1,000 g of D,L-lactic acid was introduced into a 2 L three-neck round bottom flask equipped with a stirrer. Then the mixture was reacted for one hour in an oil bath at 80° C. under heating and pressure reduction to 25 mmHg with a vacuum aspirator to remove the excessively existing water. The reaction temperature was raised to 160° C. and the reaction was conducted for 7 hours under the condition of pressure reduction to 5 to 10 mmHg, and then the reaction was terminated. As a result, 646 g of unpurified polylactic acid was obtained. The result of measurement by the following NMR analysis showed that the number average molecular weight of the prepared polylactic acid was 1,200 daltons. 750 mL of acetonitrile was added to 500 g of the prepared polylactic acid to dissolve it. 750 mL of aqueous solution of sodium hydrogen carbonate (0.1 g/mL) was slowly added thereto. The resulting mixture was stirred for 2 hours at room temperature to neutralize the polymer. 75 g of sodium chloride was added to the neutralized polymer solution for phase separation. The separated organic solvent layer was collected, and then the organic solvent was removed by fractional distillation to prepare sodium salt of polylactic acid.

NMR spectrum of the prepared sodium salt of polylactic acid is shown in FIG. 1.

<Number Average Molecular Weight Calculation from Peak Areas of $^1$H-NMR Scan>

$$\text{Number average molecular weight (daltons)} = \{(A+B)/(C/N)\} \times 72.1 \quad \text{[Equation 1]}$$

In the above equation 1,
A denotes the peak area of methylene proton of D,L-polylactic acid,
B denotes the peak area of methylene proton of terminal D,L-lactic acid of the polymer,
C denotes the peak area of methylene proton of dicarboxylic acid, and
N denotes the number of methylene protons in dicarboxylic acid.

Preparation Example 2 mPEG-PLA (Molecular Weight: 2,000-1,700 Daltons)

Figure 2:
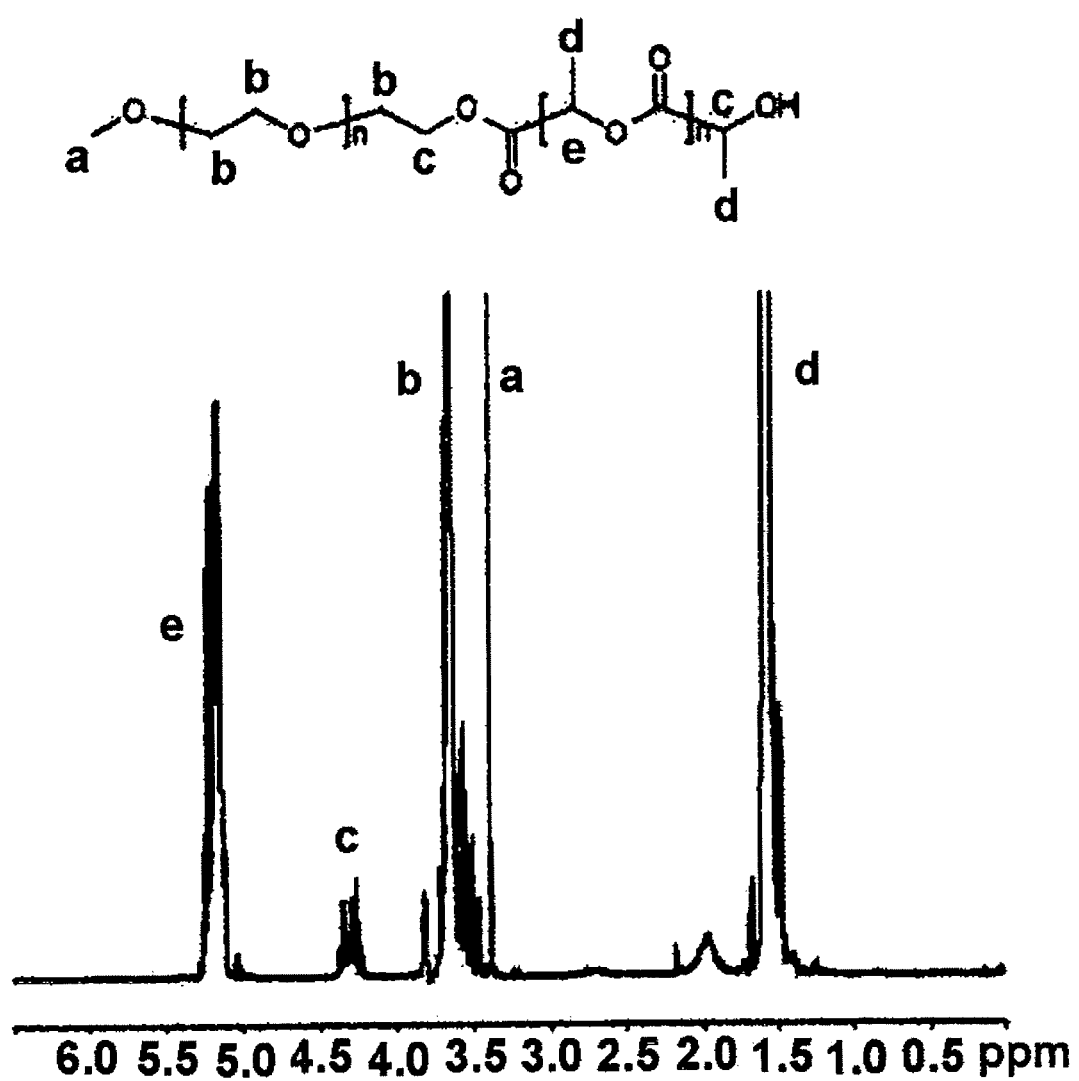
FIG. 2 is a NMR spectrum of mPEG-PLA according to Preparation Example 2.

500 g of monomethoxypolyethylene glycol (number average molecular weight: 2,000) was introduced into a 100 ml two-neck round bottom flask, and dehydrated by heating at 100° C. for 2 to 3 hours under reduced pressure. Dry nitrogen was charged in the reaction flask, and as a reaction catalyst, stannous octoate (Sn(Oct)$_2$) was added by a syringe in amount of about 0.1 wt % (1 g, 2.5 mol) with respect to D,L-lactide, the mixture was stirred for 30 minutes, and then the pressure was reduced (1 mmHg) at 130° C. for one hour to remove the solvent (toluene) used to dissolve the catalyst. 1,375 g of the purified lactide was added thereto, and the mixture was heated at 130° C. for 18 hours. The generated polymer was dissolved in methylene chloride, and diethyl ether was added thereto in order to precipitate the polymer. The obtained polymer was dried in a vacuum oven for 48 hours. The mPEG-PLA as obtained above had number average molecular weight of 2,000-1,750 daltons and was identified as the A-B type by $^1$H-NMR of FIG. 2.

Example 1

Mixed Polymeric Nanoparticle Composition of D,L-PLA-COONa/mPEG-PLA Containing Rapamycin 20 mg of rapamycin, 895 mg of mPEG-PLA of Preparation Example 2, and 329 mg of D,L-PLACOONa of Preparation Example 1 were solubilized in ethanol, and then the organic solvent was evaporated therefrom by a vacuum evaporator. To the resulting dry product, water for injection was added to make the rapamycin concentration of 2 mg/ml, thereby forming micelles. About 26 mg of divalent calcium ion was dissolved in distilled water to make the mole of calcium ion as ½ of the mole of D,L-PLACOONa, and then the resulting calcium ion solution was added dropwise to the aqueous micelle solution under stirring at 200 rpm to fix the terminal group of polylactic acid salt via the ionic bond, thereby forming the polymeric nanoparticle in which rapamycin was entrapped. The resulting solution was sterilized and filtered through 0.2 μm membrane filter, and then filled in a vial and lyophilized. The measurement results of the content of rapamycin and size of the polymeric nanoparticle in the prepared composition were as follows:
Content: 99.8%
Particle size: 19.5 nm Experiment 1

Figure 3:
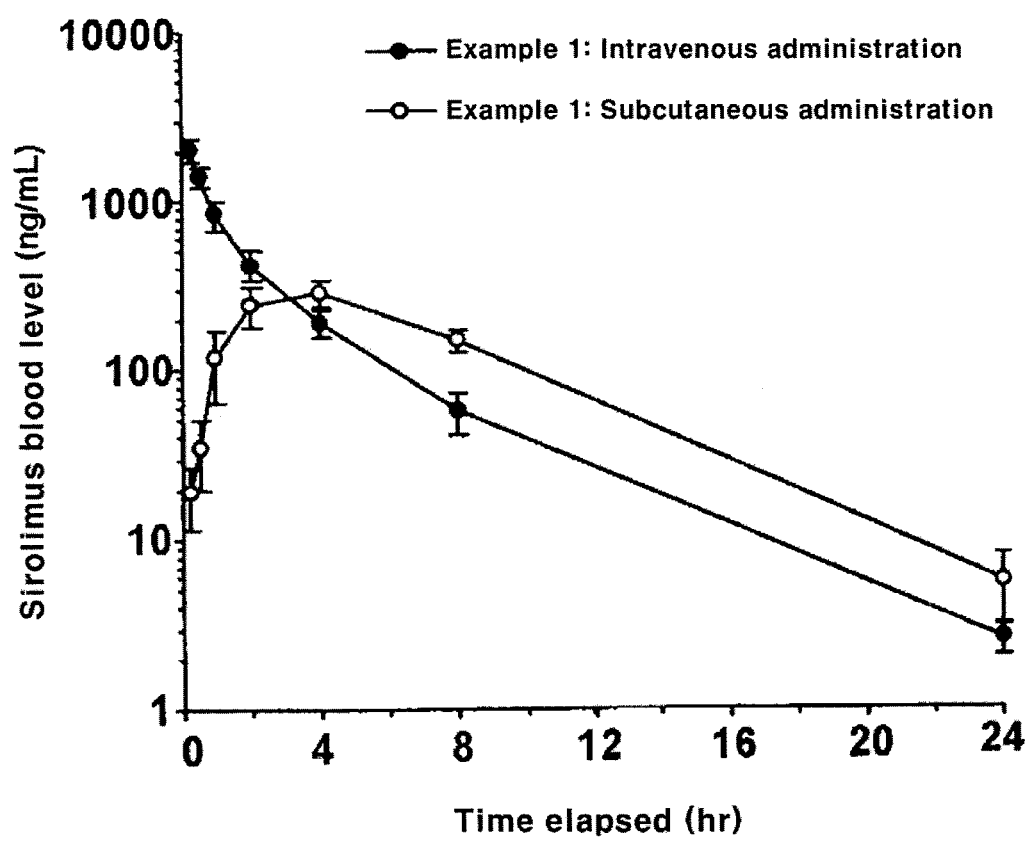
FIG. 3 is a graph obtained from Experiment 1, showing the results of in vivo pharmacokinetic test for the polymeric nanoparticles containing rapamycin.

Evaluation of In Vivo Pharmacokinetic Behavior of the Polymeric Nanoparticles Containing Rapamycin The in vivo pharmacokinetic behavior of the rapamycin-entrapping nanoparticle composition of Example 1 was evaluated. For animal experiment, male Sprague-Dawley rats weighing 210 to 250 g were used, and 0.3 ml of whole blood was taken from caudal vein every 5, 15 and 30 minutes, and 1, 2, 4, 8 and 24 hours after intravenous and subcutaneous injection of the dose of 5 mg/kg, on the basis of rapamycin. The collected whole blood was treated with the Protein Precipitation (PPT, Progress in Pharmaceutical and Biomedical Analysis, Volume 5, 2003, Pages 199-254) and then centrifuged to obtain 0.15 ml of clear supernatant which was analyzed to check the rapamycin concentration in blood by LC/MS/MS method.
(1) HPLC Conditions
  i) Analytical column: Zorbax XDB-C18 (2.1×100 mm, 3.5 mm, Agilent)
  ii) Mobile phase: 10 mM Ammonium acetate/MeOH (1/99, v/v)
  iii) Flow rate: 0.3 Ml/min
(2) Tandem Mass Spectrometry Conditions
  i) Ionization: Electro spray Ionization, Negative (ESI−)
  ii) MS Method: Multiple Reaction Monitoring (MRM)
  iii) Capillary Voltage: 2.95 kV
  iv) Cone Voltage: 134 V
  v) Collision Energy: 22 eV
  vi) Source Temperature: 100° C.
  vii) Desolvation Temperature: 200° C.
  viii) Mass Transition: Sirolimus 912.6→321.4 amu The pharmacokinetic profile of rapamycin is shown in FIG. 3, and the parameters of pharmacokinetic behavior thereof are shown in Table 1. When administered via intravenous route, the $C_{max}$ value was as high as about 7 times that of subcutaneous administration, and the half life ($t_{1/2}$) at the disappearance phase was about 3 hours, which was substantially similar to that of subcutaneous administration, but the concentration in blood at 24 hours after subcutaneous administration is as high as about 2 times that of intravenous administration. In consideration of the bioavailability (F %) in the intravenous administration as 100, the bioavailability in the subcutaneous administration was about 74%.

TABLE 1

| | Example 1 | |
|---|---|---|
| Pharmacokinetic parameters | Intravenous administration | Subcutaneous administration |
| AUC(last) (ng · hr/mL) | 3132.6 | 2304.5 |
| AUC(inf) (ng · hr/mL) | 3145.1 | 2333.3 |
| $C_{max}$ (ng/mL) | 2010.0 | 288.0 |
| $T_{max}$ (hr) | 0.25 | 4.00 |
| $t_{1/2}$ (hr) | 3.32 | 3.45 |
| F (%) | 100.0 | 73.6 |

Experiment 2

Evaluation of Radiation Sensitizing Effect of the Polymeric Nanoparticle Composition Containing Rapamycin The anticancer activity of the composition of Example 1 was examined when the composition was used in combination with radiotherapy.
Cells were taken from those stored in liquid nitrogen, and then established for in vitro cell culture. Cells were harvested, washed with sterile phosphate buffered solution (PBS), and then the number of viable cells was counted. Cells were re-suspended in sterile PBS to the level of 7×10$^7$ cells/ml.

0.1 ml of the cell suspension containing 7×10$^5$ human lung cancer cells (A549) was subcutaneously injected into the right flank of healthy nude (nu/nu) athymic mouse (20 to 25 g, 8 weeks old). A549 has been well known as a cancer which is resistant to radiotherapy and chemotherapy including some anticancer agents. After the cancer reached a certain size, heterologous graft was conducted three times to form xenografts of 3 to 4 mm. The xenograft fragments were subcutaneously injected by means of 12 gauge trocar needle into the right flank of healthy nude (nu/nu) athymic mouse (20 to 25 g, 8 weeks old). After the volume of the cancer reached 100 to 300 mm$^3$, the drug was administered, and the day was reported as Day 1. On Day 1, mice were divided into 5 groups, into which the composition of Example 1 was daily administered through caudal vein in a dose corresponding to 5 mg/kg of rapamycin for 5 days, and after 3 hours the radiation of 2 Gy was irradiated. The long axis and short axis of tumor were measured with the passage of time, and the tumor volume was calculated therefrom by means of the following math equation 1. Furthermore, in order to evaluate the therapeutic effect, the relative tumor volume was calculated according to the following math equation 2.

Tumor volume (TV)=0.5×$L$×$W^2$  [Math equation 1]

(L: long axis, W: short axis)

Relative tumor volume (RTV)=($Vt/Vo$)×100%  [Math equation 2]

(Vt: TV on Day t, Vo: TV on Day 0)

To ensure the significance of the experiment, 4 mice or more per treatment and 4 tumors or more per group were used. At the time of treatment initiation, the minimum diameter of tumor corresponded to the volume of 4 or 30 mm$^3$. Animals died within 2 weeks after the last drug administration were considered as being the cytotoxic death, and thus excluded from the evaluation. The treatment group in which there were more than 1 cytotoxic death per 3 animals or the average weight was not completely recovered after the average weight reduction in excess of 15%, was considered as showing no anticancer efficacy. The experimental result is shown in FIG. 4.

Figure 4:
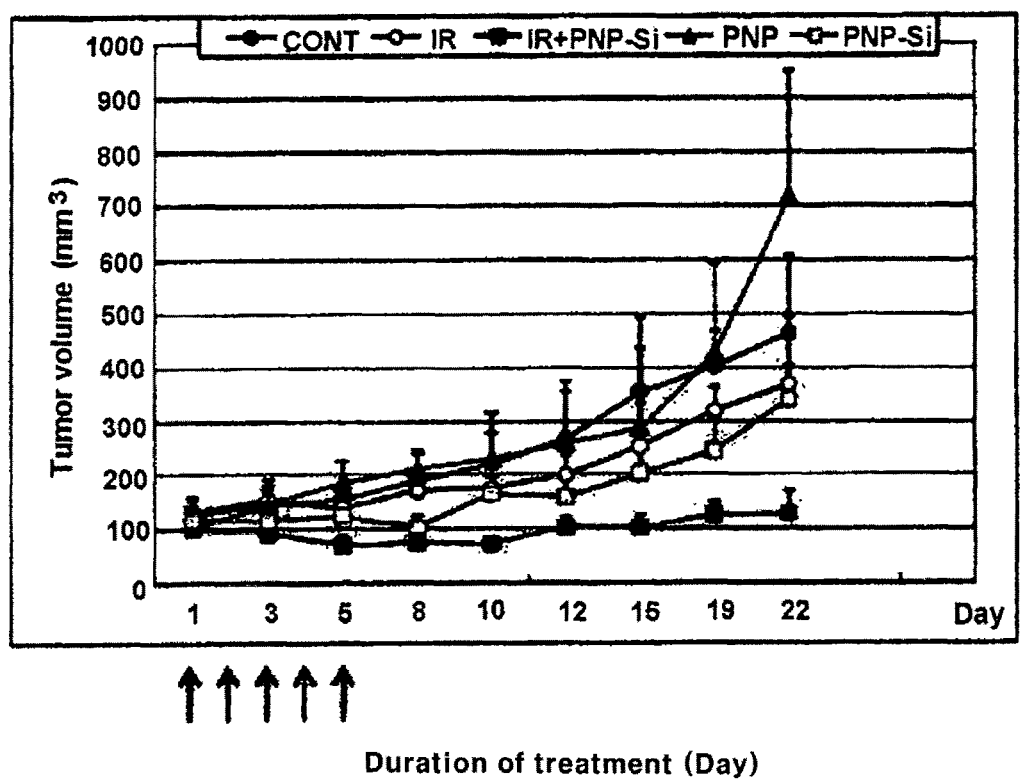
FIG. 4 is a graph obtained from Experiment 2, showing the results of radiation sensitizing effect test for the polymeric nanoparticles containing rapamycin.

As shown in FIG. 4, the anticancer efficacy in the group to which the composition of Example 1 was solely administered (PNP-Si) and the group to which radiotherapy was solely provided (IR) showed better inhibition of cancer growth as compared with the no-treatment group (CONT) and the group to which the vehicles for polymeric nanoparticles were administered (PNP). However, in the group to which the composition of Example 1 was used in combination with radiotherapy (IR+PNP-Si), greater anticancer efficacy than that in CONT and PNP groups, and even than that in PNP-Si group and IR group, were exhibited as nearly stopping the growth of cancer.

Example 2

Mixed Polymeric Nanoparticle Composition of D,L-PLA-COONa/mPEG-PLA Containing Rapamycin 25 mg of rapamycin, 1,650 mg of mPEG-PLA of Preparation Example 2, and 825 mg of D,L-PLACOONa of Preparation Example 1 were completely dissolved in dichloromethane, and then the organic solvent was evaporated by using a rotary evaporator under reduced pressure. To the resulting dry product, water for injection was added to make the rapamycin concentration of 1.0 mg/ml, thereby forming micelles. 100 mg/mL calcium chloride solution was taken to be 67.5 mg of calcium chloride, and further added to the micelles, and the mixture was stirred. The resulting solution was sterilized and filtered through 0.2 μm membrane filter, and then filled in a vial and lyophilized. The measurement results of measurement of the content of rapamycin and size of the polymeric nanoparticle in the prepared composition were as follows:

Content: 101.9%
Particle size: 19.7 nm

Experiment 3

In Vitro Evaluation of the Anticancer Activity of the Polymeric Nanoparticle Composition Containing Rapamycin To evaluate whether the effect of inhibiting proliferation of cancer cells could be kept even after rapamycin was entrapped within the polymeric nanoparticles by using the polymeric nanoparticle composition containing rapamycin of Example 2, the following experiment was conducted.

Lung cancer A549 and NCI-H460 cell lines, and breast cancer MDA-MB-231 and MCF7 cell lines were respectively incubated in DMEM (A549, MCF7) and RPMI1640 (NCI-H460, MDA-MB-231) culture solutions. One day before the treatment, each 50 cells (saline experiment group, rapamycin-free polymeric nanoparticle composition) and 100 cells (rapamycin-containing polymeric nanoparticle composition, rapamycin) were dispensed in a 6-well culture dish. The cells were cultured in an incubator for 24 hours to allow them to adhere to the bottom of the culture dish. The culture solution was removed, and the samples were diluted, respectively, to 10, 100, and 500 nM in 2 ml of fresh culture medium to treat the cells. The cells were cultured for 14 days in the incubator to obtain the cell colonies. The cells were fixed and stained with 0.5% crystal violet solution, and then the number of generated colonies was counted. The plating efficiency was calculated using the number of colonies obtained from the saline experiment group (Math equation 3).

Plating efficiency=Number of colonies in the saline treatment group/Number of cells dispended in the saline treatment group×100  [Math equation 3]

The surviving fractions in respective experiment groups were calculated by means of the following math equation 4.

Surviving fraction=Number of colonies in the treatment group/(Number of cells dispended in the treatment group×Plating efficiency/100)  [Math equation 4]

Figure 5:
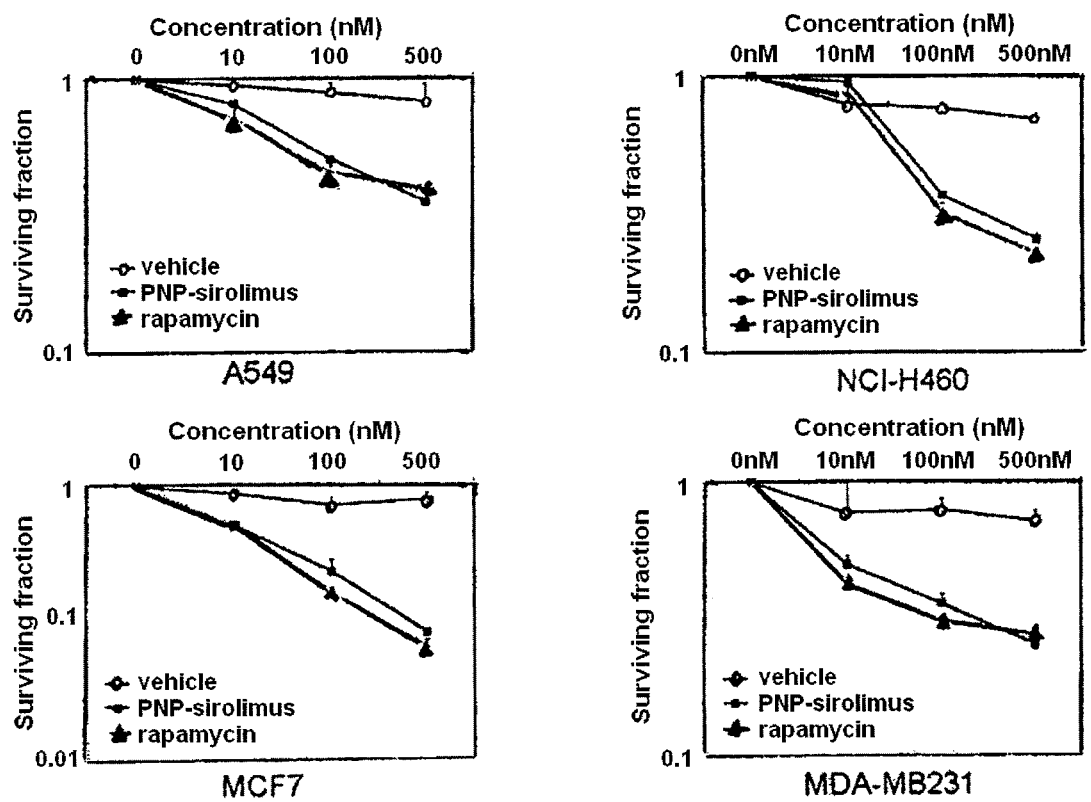
FIG. 5 is a graph obtained from Experiment 3, showing the results of in vitro anti-cancer activity test for the polymeric nanoparticles containing rapamycin.

The results of experiment are shown in FIG. 5.

With reference to the result shown in FIG. 5, it was confirmed that the rapamycin-free polymeric nanoparticle vehicles had substantially no effect on the proliferation ability of cells, and the rapamycin-containing polymeric nanoparticle composition (PNP-sirolimus) remarkably decreased the proliferation ability of cells as in the use of rapamycin itself. This result means that rapamycin can maintain its pharmacological effect even though it is entrapped within the polymeric nanoparticles.

Experiment 4

Evaluation of In Vivo Pharmacokinetic Behavior of the Polymeric Nanoparticles Containing Rapamycin The in vivo pharmacokinetic behavior of the rapamycin-entrapping nanoparticle composition of Example 2 was evaluated by means of the same method as in Experiment 1. However, the composition was administered via oral, intravenous or subcutaneous route in the dose of 10 mg/kg on the basis of rapamycin, and 0.3 ml of whole blood was taken from caudal vein every 15 and 30 minutes, and 1, 2, 4, 8, 24 and 48 hours after administration.

Figure 6:
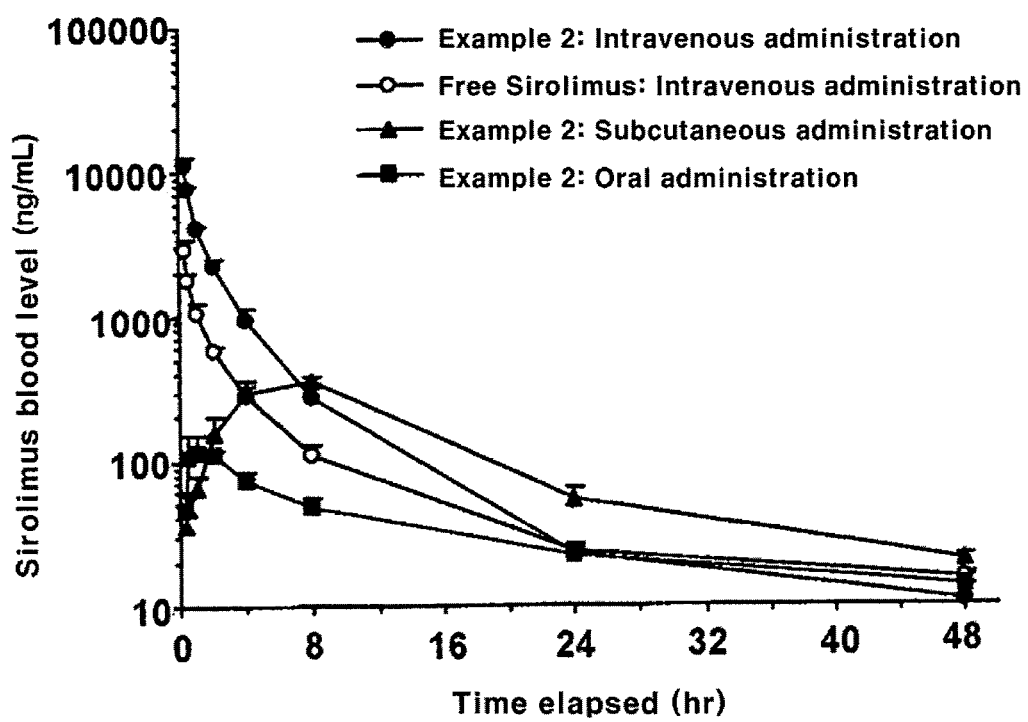
FIG. 6 is a graph obtained from Experiment 4, showing the results of in vivo pharmacokinetic test for the polymeric nanoparticles containing rapamycin.

The analysis results of rapamycin level in blood are shown in FIG. 6, and the parameters of pharmacokinetic behavior are shown in Table 2.

TABLE 2

| Pharmacokinetic parameters | Free sirolimus Intravenous administration | Example 2 Intravenous administration | Example 2 Subcutaneous administration | Example 2 Oral administration |
|---|---|---|---|---|
| AUC(last) (ng · hr/mL) | 5366.7 | 16901.7 | 5275.2 | 1559.8 |
| AUC(inf) (ng · hr/mL) | 5597.5 | 16991.2 | 5576.4 | 1983.7 |
| $C_{max}$ (ng/mL) | 2890 | 11303.3 | 350 | 129.7 |
| $T_{max}$ (hr) | 0.25 | 0.25 | 8.00 | 1.17 |
| $t_{1/2}$ (hr) | 10.48 | 5.68 | 10.14 | 21.27 |
| F (%) | 100 | 315 | 98 | 29 |

AUC of the composition of Example 2 as intravenously administered was as high as 3 times AUC of rapamycin itself, and therefore it can be seen that the polymeric nanoparticle composition of the present invention has a blood retention property. The fact that a particulate drug delivery system has the blood retention property means that the system has the accumulative property in cancer tissue due to EPR (Enhanced Permeability and Retention) effect, and the same effect can be obtained even with a lower dose.

When the composition of Example 2 is subcutaneously administered, the bioavailability (BA %) was 100%. AUC was about 33% level of intravenous administration, but the blood levels at 24 and 48 hours were about 2 times or more. That is, the level was persistently maintained above the effective level for a long period. When administered via oral route, the bioavailability was shown as about 30%, meaning that the composition of the present invention shows higher bioavailability as compared with the known oral formulations (less than 20%).

Experiment 5

Evaluation of the Anticancer Efficacy of the Rapamycin-Containing Polymeric Nanoparticle Composition in Cancer-Transplanted Animal Model The anticancer efficacy of the rapamycin-containing polymeric nanoparticle composition of Example 2 in animal model was evaluated as follows.

Lung cancer cell lines A549 cells were cultured in DMEM medium. The cells were harvested, washed with sterile phosphate buffered solution (PBS), and then counted. 0.1 ml of the suspension containing $1\times10^6$ A549 cells was subcutaneously injected into right thigh of healthy nude (nu/nu) athymic mouse (20 to 25 g, 6 weeks old). After 3 weeks, when the tumor size reached about 70 mm³, mice were divided into five groups, and the day was recorded as Day 1. From this point of time, each of the rapamycin-containing polymer micelle composition and the rapamycin-free polymer micelle composition was intravenously administered into caudal vein of the respective experiment groups in a dose of 20 mg/kg. From Day 1, the long axis and short axis of tumor were measured two times per week, and the tumor volume was calculated therefrom by means of the following math equation 5. At the same time of measurement of the tumor volumes, the weights of mice were also measured.

Tumor volume=0.5×(Length of long axis)×(Length of short axis)²     [Math equation 5]

Figure 7:
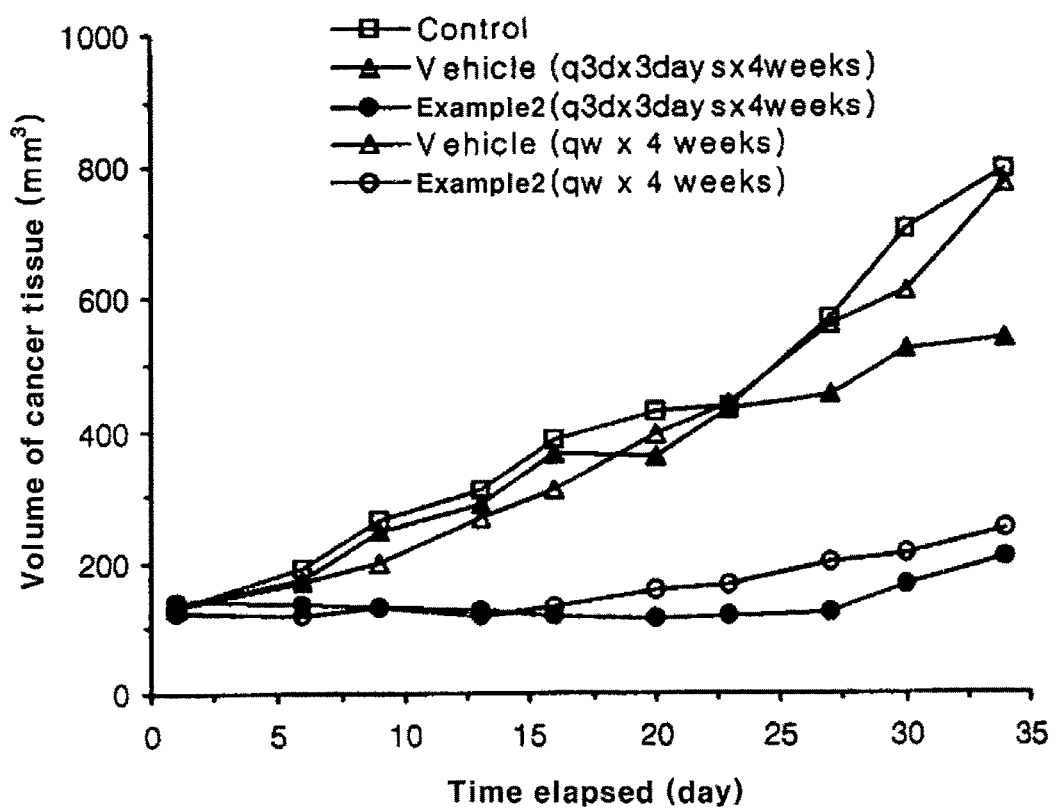
FIG. 7 is a graph obtained from Experiment 5, showing the results of anti-cancer efficacy test in animal model for the polymeric nanoparticles containing rapamycin.

As shown in FIG. 7, the rapamycin-containing polymeric nanoparticle composition showed a remarkable effect of delaying the growth of A549 cancer, as compared with the control group and the vehicle group. The group to which the composition was administered three times per week for 4 weeks (q3d×3 days×4 weeks) showed a slightly better anticancer efficacy as compared with the group to which the composition was administered once a week for 4 weeks (qw×4 weeks), but there was no significant difference between the two groups. From this, in consideration of a possibility of expressing toxicity upon excessive administration of the drug, it is concluded that the formulation according to the present invention can exhibit the efficacy even at a lower dose. Meanwhile, the change in weight of mouse upon administration of the drug was less than 10%, showing a tendency of recovery after completion of the administration. Such recovery was retarded in the group to which the drug was administered three times per week for 4 weeks, as compared with the group to which the drug was administered once a week for 4 weeks.

Experiment 6

Figure 8:
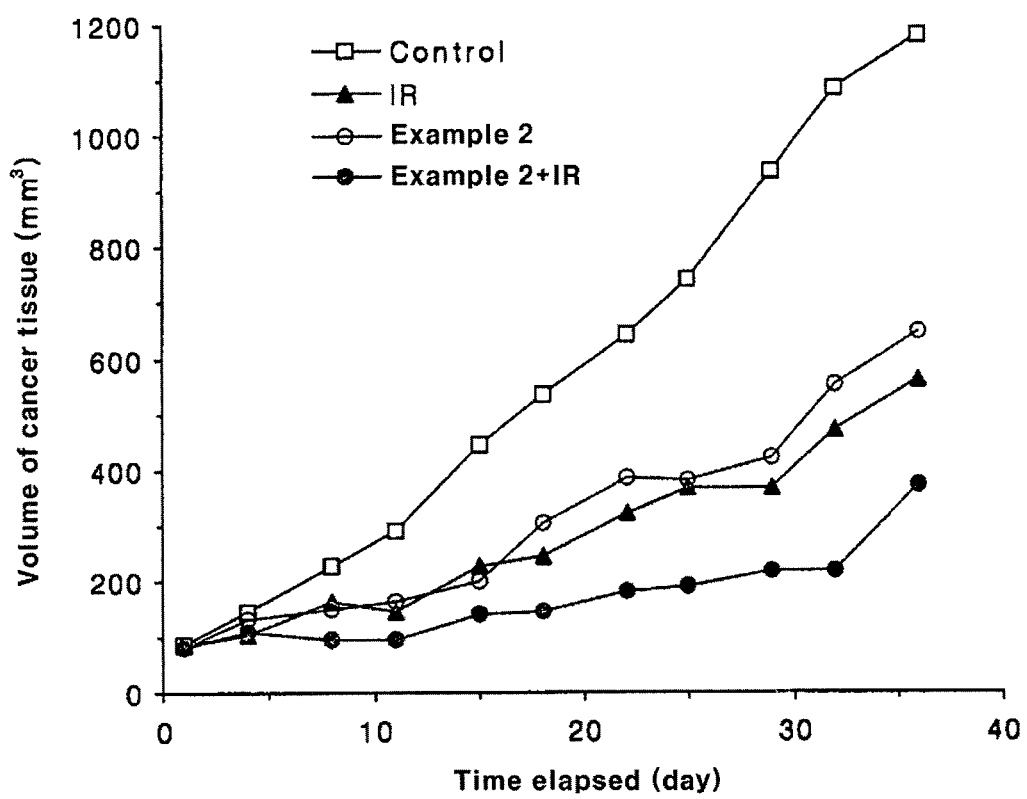
FIG. 8 is a graph obtained from Experiment 6, showing the results of radiation sensitizing effect test in animal model for the polymeric nanoparticles containing rapamycin.

Evaluation of Radiation Sensitizing Effect of the Polymeric Nanoparticle Composition Containing Rapamycin The anticancer activity of the composition of Example 2 was evaluated when the composition was used in combination with radiotherapy. The experimental result is shown in FIG. 8. Differently from Experiment 2, the present experiment daily administered the composition in a dose of 5 mg/kg only for 5 days, and then compared the irradiated group (2 Gy treatment) with the non-irradiated group.

As shown in FIG. 8, the group to which the composition of Example 2 was solely administered (Example 2) and the group to which radiotherapy was solely applied (IR) provided better anticancer efficacy as compared with the control group, and there was no significant difference between the Example 2 group and the IR group. However, the group to which the composition of Example 2 was administered and after 3 hours the radiation of 2 Gy was applied (Example 2+IR) showed higher level of inhibition of cancer growth as compared with all of the control groups.

The invention claimed is:

1. A method for treating cancer in a combination therapy with radiation comprising administering to a subject in need thereof a therapeutically effective amount of an injectable composition comprising polymeric nanoparticles containing rapamycin, wherein the composition comprises:
    (i) an A-B type diblock copolymer having a hydrophilic block (A) of methoxy polyethylene glycol and a hydrophobic block (B) of polylactic acid, (ii) an alkali metal salt of polylactic acid or its derivative having at least one carboxyl group on its end, and
(iii) rapamycin as an active ingredient,
wherein rapamycin is entrapped within the micelle formed from the A-B type diblock copolymer and the alkali metal salt of polylactic acid or its derivative,
wherein the composition is reconstituted to the rapamycin concentration of 0.1 to 25 mg/ml, and
wherein the composition is administered at the time of, before or after irradiation to mammalian cancer cell to increase a sensitivity of mammalian cancer cell to radiotherapy.

2. The method according to claim 1, wherein the number average molecular weight of the hydrophilic block (A) of the diblock copolymer is 500 to 20,000 daltons, the number average molecular weight of the hydrophobic block (B) of the diblock copolymer is 500 to 10,000 daltons, and the content of the hydrophilic block (A) in the diblock copolymer is 40 to 70 wt % on the basis of total 100 wt % of the diblock copolymer.

3. The method according to claim 1, wherein the polylactic acid or its derivative having at least one carboxyl group on its end is one or more selected from the group consisting of polylactic acid, polylactide, polyglycolide, polymandelic acid, polycaprolactone, polyanhydride and copolymers thereof, and its number average molecular weight is 500 to 2,500 daltons.

4. The method according to claim 1, wherein the alkali metal is one or more monovalent metals selected from the group consisting of sodium, potassium and lithium.

5. The method according to claim 1, wherein the composition further comprises divalent or trivalent metal ion.

6. The method according to claim 5, wherein the divalent or trivalent metal ion is divalent or trivalent cation of the metal selected from the group consisting of calcium, magnesium, barium, chrome, iron, manganese, nickel, copper, zinc and aluminum.

7. The method according to claim 1, wherein the weight ratio of the A-B type diblock copolymer and the alkali metal salt of polylactic acid or its derivative having at least one carboxyl group on its end is 9:1 to 3:7.

8. The method according to claim 1, wherein the composition is administered at a timing of 1 minute to 7 days before irradiation.

9. The method according to claim 1, wherein chemotherapy in combination with radiotherapy is practiced 1 to 5 times per week over a period of 4 to 12 weeks.

* * * * *